(12) United States Patent
Yonehara et al.

(10) Patent No.: US 7,432,072 B2
(45) Date of Patent: *Oct. 7, 2008

(54) METHOD OF PREVENTING WRONG COLOR FORMATION OF N-(CARBOXYMETHYLAMINOCARBONY)-4,4'-BIS(DIMETHYLAMINO) DIPHENYLAMINE SODIUM, REAGENT SOLUTION FOR THE METHOD, AND MEASUREMENT METHOD EMPLOYING THE METHOD

(75) Inventors: Satoshi Yonehara, Kyoto (JP); Tsuguki Komori, Gujo-gun (JP)

(73) Assignee: Arkray, Inc., Kyoto (JP)

( * ) Notice: Subject to any disclaimer, the term of this patent is extended or adjusted under 35 U.S.C. 154(b) by 210 days.

This patent is subject to a terminal disclaimer.

(21) Appl. No.: 10/514,382

(22) PCT Filed: May 2, 2003

(86) PCT No.: PCT/JP03/05642

§ 371 (c)(1),
(2), (4) Date: Nov. 12, 2004

(87) PCT Pub. No.: WO03/097865

PCT Pub. Date: Nov. 27, 2003

(65) Prior Publication Data

US 2005/0176086 A1    Aug. 11, 2005

(30) Foreign Application Priority Data

May 21, 2002    (JP) ............................. 2002-146522

(51) Int. Cl.
*C12Q 1/26*    (2006.01)
*C07D 257/00*    (2006.01)

(52) U.S. Cl. ......................................... 435/25; 58/253
(58) Field of Classification Search ........................ None
See application file for complete search history.

(56) References Cited

U.S. PATENT DOCUMENTS

2002/0025546 A1    2/2002    Komori et al.
2003/0186449 A1 *  10/2003   Yonehara et al. .............. 436/66
2004/0063213 A1    4/2004    Hirai et al.
2004/0209378 A1    10/2004   Horii et al.
2005/0042709 A1 *  2/2005    Yonehara et al. .............. 435/25

FOREIGN PATENT DOCUMENTS

| EP | 1 002 874 | 5/2000 |
| JP | 6-197793 | 7/1994 |
| JP | 6-197794 | 7/1994 |
| WO | 02/27331 | 4/2002 |
| WO | WO0227330 A1 * | 4/2002 |
| WO | 03/033730 | 4/2003 |

OTHER PUBLICATIONS

Sakurabayashi et al. New Enzyme Assay for Glycohemoglobin; Clinical Chemistry, vol. 49, No. 2 (2003) pp. 269-274.*
Markus et al. The Solution Structure of Ribosomal Protein S4 Delta 41 Reveals Two Subdomains and a Positively Charged Surface That May Interact With RNA; The EMBO Journal, vol. 17, No. 16 (1998) pp. 4559-4571.*
Harvath. Enhancement of Granulocyte Chemiluminescence With Hydroxyl Radical Scavengers; Infection and Immunity, vol. 25, No. 1 (1979) pp. 473-476.*

* cited by examiner

*Primary Examiner*—Jon P Weber
*Assistant Examiner*—Paul C. Martin
(74) *Attorney, Agent, or Firm*—Hamre, Schumann, Mueller & Larson, P.C.

(57) ABSTRACT

The present invention provides a method of preventing erroneous color development of N-(carboxymethylaminocarbonyl)-4,4'-bis(dimethylamino)diphenylamine sodium salt as a color-developing substrate, thereby improving the accuracy of measurement utilizing a redox reaction performed using the color-developing substrate. A tetrazolium compound, sodium azide, and the color-developing substrate are added to a sample in the presence of a surfactant. A reaction between an oxidizing substance derived from an analyte in the sample and the color-developing substrate, which develops color by oxidation, is caused by an oxidoreductase. By measuring the color developed, the amount of the oxidizing substance is determined. The concentrations of the respective components in the reaction solution are set so that 0.01 to 1 mmol of the tetrazolium compound, 0.003 to 0.5 mmol of the sodium azide, and 0.006 to 0.4 mmol of the surfactant are present per μmol of the color-developing substrate, and the pH of the reaction solution is set in the range from 6 to 9.

10 Claims, 1 Drawing Sheet

METHOD OF PREVENTING WRONG COLOR FORMATION OF N-(CARBOXYMETHYLAMINOCARBONY)-4,4'-BIS(DIMETHYLAMINO) DIPHENYLAMINE SODIUM, REAGENT SOLUTION FOR THE METHOD, AND MEASUREMENT METHOD EMPLOYING THE METHOD

This application is a 371 of PCT/JP03/05642 filed May 2, 2003.

TECHNICAL FIELD

The present invention relates to a method of preventing erroneous color development of N-(carboxymethylaminocarbonyl)-4,4'-bis(dimethylamino)diphenylamine sodium salt, and to a reagent solution and a measurement method utilizing a redox reaction using the method.

BACKGROUND ART

Conventionally, the measurement of the amount of an analyte in a sample using a redox reaction has been utilized for a wide range of applications. For example, such measurement is carried out in the following manner. First, a peroxidase (hereinafter referred to as "POD") and a reducing agent are added to an oxidizing substance as an analyte or to an oxidizing substance formed from an analyte, so that a redox reaction occurs between the oxidizing substance and the reducing agent with the POD as a catalyst. When a reducing agent that develops color when it is oxidized is used as the reducing agent, the amount of the oxidizing substance can be determined by measuring the color developed because there is a correlation between the amount of the color developed and the amount of the oxidizing substance. As the reducing agent that develops color when it is oxidized, N-(carboxymethylaminocarbonyl)-4,4'-bis(dimethylamino)diphenylamine sodium salt has been used.

However, such a method does not exhibit sufficient measurement sensitivity and thus may fail to improve the accuracy of the measurement.

DISCLOSURE OF INVENTION

In light of the above-described problem, the inventors of the present invention conducted in-depth researches and found out that the measurement sensitivity can be improved by carrying out the redox reaction in the presence of a tetrazolium compound and sodium azide. This finding was already filed as another patent application. However, the inventors of the present invention further found that, although such a measurement method can improve the measurement sensitivity as described above, it brings about another problem that erroneous color development of N-(carboxymethylaminocarbonyl)-4,4'-bis(dimethylamino)diphenylamine sodium salt as a substrate that develops color (hereinafter referred to as a "color-developing substrate") may occur prior to the redox reaction due to the presence of the N-(carboxymethylaminocarbonyl)-4,4'-bis(dimethylamino)diphenylamine sodium salt, the tetrazolium compound, and the sodium azide together in the solution. Such erroneous color development leads to an increase in background in the above-described measurement of the color developed and, in some cases, to a shortage of the color-developing substrate in the redox reaction even though the amount of the color-developing substrate added is sufficient.

Therefore, it is an object of the present invention to provide a method of preventing erroneous color development of N-(carboxymethylamino carbonyl)-4,4'-bis(dimethylamino) diphenylamine sodium salt.

In order to achieve the above object, the present invention provides a method of preventing erroneous color development of N-(carboxymethylamino carbonyl)-4,4'-bis(dimethylamino)diphenylamine sodium salt (hereinafter also referred to as "DA-64") in an aqueous solvent containing a tetrazolium compound and sodium azide, including: mixing a tetrazolium compound, sodium azide, and DA-64 in an aqueous solvent in the presence of a surfactant, wherein 0.01 to 1 mmol of the tetrazolium compound, 0.003 to 0.5 mmol of the sodium azide, and 0.006 to 0.4 mmol of the surfactant are present per µmol of the DA-64, and a pH of the aqueous solvent containing the DA-64, the tetrazolium compound, the sodium azide, and the surfactant is in a range from 6 to 9.

By mixing the above-described three components in the presence of the surfactant and setting the concentrations of the respective components and the pH of the mixture in the above-described ranges, the above-described erroneous color development of the DA-64 can be suppressed even though the "DA-64, tetrazolium compound, and sodium azide" are present together in the aqueous solvent. Thus, if such a method of preventing the erroneous color development is applied to a measurement using a redox reaction described later, an increase in background absorbance in the measurement of an absorbance can be suppressed so that an analyte can be measured with high accuracy. The order of adding the respective components is not particularly limited as long as the surfactant is present when all of the DA-64, the tetrazolium compound, and the sodium azide are mixed with each other in the aqueous solvent. Thus, for example, the surfactant may be added to the aqueous solvent in advance and then the remaining three components may be added to the aqueous solvent, separately. Alternatively, after the tetrazolium compound and the sodium azide have been added to the aqueous solvent, the DA-64 may be added in the presence of the surfactant. These examples are for illustration only, and the order of adding the components is not limited to these examples.

Next, the present invention provides a DA-64 reagent solution including DA-64, a tetrazolium compound, sodium azide, and a surfactant, wherein 0.01 to 1 mmol of the tetrazolium compound, 0.003 to 0.5 mmol of the sodium azide, and 0.006 to 0.4 mmol of the surfactant are present per µmol of the DA-64, and a pH of the reagent solution is in a range from 6 to 9.

In the reagent solution having such a composition, the erroneous color development of the DA-64 also can be prevented even in the presence of the tetrazolium compound and the sodium azide, as in the case of the above-described method of preventing the erroneous color development. Thus, it becomes possible to store DA-64 stably in the form of a solution, and such a reagent solution suitably is used for a measurement method described below and the like, for example.

Next, the present invention provides a method of measuring an oxidizing substance derived from an analyte in a sample, including: causing a reaction between the oxidizing substance derived from the analyte and DA-64 as a color-developing substrate, the reaction being caused by an oxidoreductase in the presence of a tetrazolium compound and sodium azide; and determining an amount of the oxidizing substance by measuring the color developed by the color-developing substrate. In this method, the tetrazolium compound, the sodium azide, and the color-developing substrate are mixed in an aqueous solvent in the presence of a surfactant so that 0.01 to 1 mmol of the tetrazolium compound, 0.003 to 0.5 mmol of the sodium azide, and 0.006 to 0.4 mmol of the surfactant are present per μmol of the DA-64 as the color-developing substrate, and a pH of the resultant mixture is in a range from 6 to 9.

Such a measurement method is excellent not only in measurement sensitivity but also in measurement accuracy because an increase in background due to the erroneous color development of the DA-64 can be suppressed. In the present invention, "an oxidizing substance derived from an analyte" includes the analyte itself, an oxidizing substance contained in the analyte, and an oxidizing substance formed from the analyte using an oxidoreductase or the like.

In the measurement method according to the present invention, the aqueous solvent preferably is a sample solution containing the analyte. For example, it is preferable that the tetrazolium compound and the sodium azide are added to the sample solution and thereafter, the N-(carboxymethylamino carbonyl)-4,4'-bis(dimethylamino)diphenylamine sodium salt (DA-64) and the oxidoreductase further are added to the sample solution in the presence of the surfactant to cause the reaction by the oxidoreductase.

In the measurement method according to present invention, the type of the sample is not particularly limited. The method also can be applied to samples other than whole blood, plasma, serum, and blood cells, e.g., biological samples such as urine and spinal fluid, drinks such as juices, and foods such as soy sauce and Worcestershire sauce.

In the measurement method according to present invention, the analyte is not particularly limited, as long as a redox reaction is utilized. For example, the analyte may be components in whole blood, components in erythrocytes, components in plasma, components in serum, components in urine, components in spinal fluid, and the like, and it preferably is a component in erythrocytes. For example, when a component in erythrocytes is to be measured, whole blood itself may be hemolyzed to prepare a sample, or erythrocytes may be separated from whole blood and hemolyzed to prepare a sample. Specific examples of the analyte include glycated proteins such as glycated hemoglobin and glycated albumin, glycated peptides, glycated amino acids, glucose, uric acid, cholesterol, creatinine, sarcosine, and glycerol. Among these, glycated proteins are more preferable and glycated hemoglobin is particularly preferable. The reason for this is as follows. Glycated hemoglobin has been regarded as an important indicator in the diagnosis, therapy, and the like of diabetes, because it reflects the patient's past history of blood glucose levels. Since the amount of glycated hemoglobin can be measured accurately according to the present invention, the reliability of glycated hemoglobin as the indicator is improved. Thus, the present invention is beneficial in the field of clinical medicine and the like.

In the measurement method of the present invention, when the analyte is a glycated protein, it is preferable that a glycation site thereof is degraded by oxidation with a fructosyl amino acid oxidase (hereinafter referred to as "FAOD") so that hydrogen peroxide is formed. Also, when the analyte is a glycated peptide or a glycated amino acid, it is preferable that the glycated peptide or the glycated amino acid similarly is subjected to the action of a FAOD. The hydrogen peroxide thus formed corresponds to the above-described oxidizing substance derived from the analyte. Moreover, it is preferable that glycated proteins and glycated peptides are treated with a protease prior to the FAOD treatment as necessary.

As the FAOD, a FAOD catalyzing a reaction represented by Formula (1) below preferably is used.

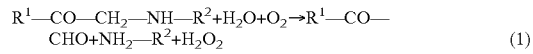

In Formula (1), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by

where n is an integer of 0 to 6.

In Formula (1), $R^2$ is not particularly limited. However, when the substrate is a glycated amino acid, a glycated peptide, or a glycated protein, for example, there is a difference between the case where an α-amino group is glycated and the case where an amino group other than the α-amino group is glycated.

In Formula (1), when an α-amino group is glycated, $R^2$ is an amino acid residue or a peptide residue represented by Formula (2) below.

$$—CHR^3—CO—R^4 \quad (2)$$

In Formula (2), $R^3$ denotes an amino-acid side chain group. $R^4$ denotes a hydroxyl group, an amino acid residue, or a peptide residue, and can be represented, for example, by Formula (3) below. In Formula (3), n is an integer of 0 or more, and $R^3$ denotes an amino-acid side chain group as in the above.

$$—(NH—CHR^3—CO)_n—OH \quad (3)$$

In Formula (1), when an amino group other than the α-amino group is glycated (i.e., an amino-acid side chain group is glycated), $R^2$ can be represented by Formula (4) below.

In Formula (4), $R^5$ denotes a portion other than the glycated amino group in the amino-acid side chain group. For example, when the glycated amino acid is lysine, $R^5$ is as follows.

For another example, when the glycated amino acid is arginine, $R^5$ is as follows.

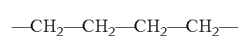

In Formula (4), $R^6$ denotes hydrogen, an amino acid residue, or a peptide residue, and can be represented, for example, by Formula (5) below. In Formula (5), n denotes an integer of 0 or more, and $R^3$ denotes an amino-acid side chain group as in the above.

$$—(CO—CHR^3—NH)_n—H \quad (5)$$

In Formula (4), $R^7$ denotes a hydroxyl group, an amino acid residue, or a peptide residue, and can be represented, for example, by Formula (6) below. In Formula (6), n is an integer of 0 or more, and $R^3$ denotes an amino-acid side chain group as in the above.

$$—(NH—CHR^3—CO)_n—OH \quad (6)$$

As the FAOD, a commercially available product named Fructosyl-Amino Acid Oxidase (FAOX-E) (manufactured by Kikkoman Corporation) specific for a glycated amino acid having a glycated α-amino group, commercially available products named FOD (manufactured by Asahi Chemical Industry Co., Ltd.) and KAO (manufactured by Genzyme Japan K.K.) specific for a glycated amino acid having a glycated α-amino group and for a glycated amino acid such as lysine having a glycated ε-amino group, and the like may be used, for example.

BEST MODE FOR CARRYING OUT THE INVENTION

Figure 1:
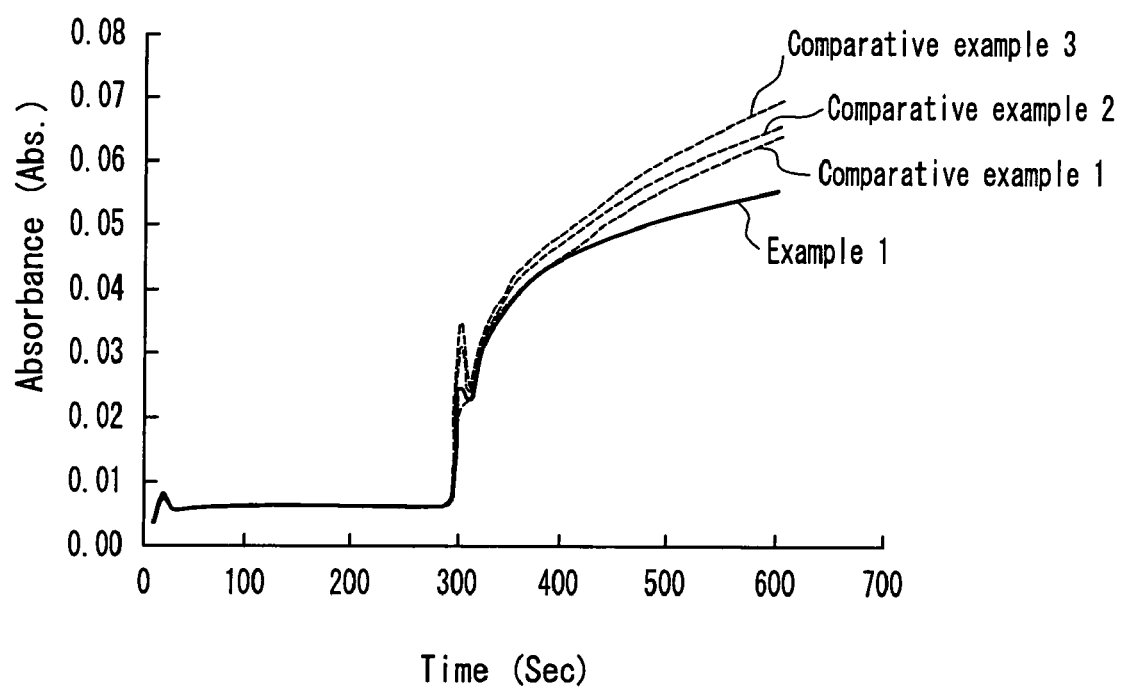
FIG. 1 is a graph showing the change in absorbance with time in one example of a measurement method according to the present invention.

The present invention prevents the erroneous color development of DA-64 in the following manner, for example.

First, a surfactant is dissolved in an aqueous solvent, and then a tetrazolium compound, sodium azide, and DA-64 are mixed with the resultant solution. The tetrazolium compound, the sodium azide, and the DA-64 are mixed so that 0.01 to 1 mmol of the tetrazolium compound, 0.003 to 0.5 mmol of the sodium azide, and 0.006 to 0.4 mmol of the surfactant are present per μmol of the DA-64, and the pH of the mixture is adjusted so as to be in the range from 6 to 9.

Preferably, 0.02 to 0.8 mmol of the tetrazolium compound, 0.01 to 0.3 mmol of the sodium azide, and 0.01 to 0.4 mmol of the surfactant are present per μmol of the DA-64. Particularly preferably, 0.03 to 0.6 mmol of the tetrazolium compound, 0.01 to 0.2 mmol of the sodium azide, and 0.04 to 0.3 mmol of the surfactant are present per μmol of the DA-64. Furthermore, the pH of the mixture preferably is in the range from 6 to 9, more preferably from 6.5 to 8.

As described above, the order of adding the respective components is not particularly limited, as long as the surfactant falling within the above-described concentration range is present when mixing the remaining three components: the tetrazolium compound, the sodium azide, and the DA-64.

The type of the aqueous solvent is not particularly limited, and water, various buffers, and the like can be used, for example. Examples of the buffers include Tris-HCl, sodium phosphate, EPPS, HEPES, and TES buffers. Among these, Tris-HCl and sodium phosphate buffers are preferable. Furthermore, the concentration of the buffer is, for example, in the range from 10 to 300 mmol/l, preferably from 50 to 300 mmol/l.

The surfactant is not particularly limited, and may be, for example, polyoxyethylene alkyl ether such as Brij 35, Brij 58, and polyoxyethylene lauryl ether, polyoxyethylene alkylphenyl ether such as Triton X-100 and Triton X-114, polyoxyethylene sorbitan ether such as Tween 20 and Tween 60, and the like.

The tetrazolium compound preferably has substituents with a ring structure (ring substituents) at least at two positions on its tetrazole ring, more preferably at three positions on its tetrazole ring, for example.

In the case where the tetrazolium compound has ring substituents at least at two positions on its tetrazole ring as described above, it is preferable that the ring substituents are at the 2-position and 3-position on the tetrazole ring. Further, in the case where the tetrazolium compound has ring substituents at three positions on its tetrazole ring, it is preferable that the ring substituents are at the 2-position, 3-position, and 5-position on the tetrazole ring.

Further, it is preferable that at least two ring substituents of the tetrazolium compound have a benzene ring structure. Other than the benzene ring structure, the ring substituents may have a resonance structure with S or O being contained in the ring skeleton, for example. Examples of the ring substituents with such a resonance structure include a thienyl group, thiazoyl group, and the like.

Furthermore, it is preferable that the tetrazolium compound has ring substituents at least at three positions on its tetrazole ring and at least two of the ring substituents have a benzene ring structure.

Still further, it is preferable that at least one ring substituent has a functional group, and a larger number of functional groups are more preferable.

Preferable examples of the functional group include electron-withdrawing functional groups such as a halogen group, ether group, ester group, carboxy group, acyl group, nitroso group, nitro group, hydroxy group, and sulfo group. Examples other than these functional groups include characteristic groups containing oxygen such as a hydroperoxy group, oxy group, epoxy group, epidioxy group, and oxo group; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, and isothiocyanate group. Among these electron-withdrawing functional groups, a nitro group, sulfo group, halogen group, carboxy group, hydroxy group, methoxy group, ethoxy group are preferable. Examples other than the above-described electron-withdrawing functional groups include unsaturated hydrocarbon groups such as a phenyl group ($C_6H_5$—) and styryl group ($C_6H_5CH=CH$—). It is to be noted that the functional groups may have been ionized by dissociation.

Still further, it is preferable that the tetrazolium compound has benzene rings at the 2-position and 3-position on its tetrazole ring and at least one of the benzene rings has at least one functional group selected from the group consisting of a halogen group, carboxy group, nitro group, hydroxy group, sulfo group, methoxy group, and ethoxy group. It is to be noted here that both the benzene rings may have such a functional group. Further, the functional group may be at any positions (ortho-, meta-, pra-) on each of the benzene rings. Furthermore, the number of the functional groups is not particularly limited, and the benzene ring may have either the same or different functional groups.

Examples of the tetrazolium compound having ring substituents with a benzene ring structure at the 2-position, 3-position, and 5-position on its tetrazole ring include:

2-(4-iodophenyl)-3-(4-nitrophenyl)-5-(2,4-disulfophenyl)-2H-tetrazolium salt;

2-(4-iodophenyl)-3-(2,4-dinitrophenyl)-5-(2,4-disulfophenyl)-2H-tetrazolium salt;

2-(2-methoxy-4-nitrophenyl)-3-(4-nitrophenyl)-5-(2,4-disulfophenyl)-2H-tetrazolium salt;

2-(4-iodophenyl)-3-(4-nitrophenyl)-5-phenyl-2H-tetrazolium salt;

3,3'-(1,1'-biphenyl-4,4'-diyl)-bis(2,5-diphenyl)-2H-tetrazolium salt;

3,3'-[3,3'-dimethoxy-(1,1'-biphenyl)-4,4'-diyl]-bis[2-(4-nitrophenyl)-5-phenyl-2H-tetrazolium salt];

2,3-diphenyl-5-(4-chlorophenyl)tetrazolium salt;

2,5-diphenyl-3-(p-diphenyl)tetrazolium salt;

2,3-diphenyl-5-(p-diphenyl)tetrazolium salt;

2,5-diphenyl-3-(4-styrylphenyl)tetrazolium salt;

2,5-diphenyl-3-(m-tolyl)tetrazolium salt; and
2,5-diphenyl-3-(p-tolyl)tetrazolium salt.

The tetrazolium compound is not limited to those described above. In addition to the above-described tetrazolium compounds, tetrazolium compounds having ring substituents with a benzene ring structure at two positions and one ring substituent with a structure other than the benzene ring structure at one position on its tetrazole ring also may be used. Examples of such tetrazolium compounds include:
2,3-diphenyl-5-(2-thienyl)tetrazolium salt;
2-benzothiazoyl-3-(4-carboxy-2-methoxyphenyl)-5-[4-(2-sulfoethyl carbamoyl)phenyl]-2H-tetrazolium salt;
2,2'-dibenzothiazoyl-5,5'-bis[4-di(2-sulfoethyl)carbamoylphenyl]-3,3'-(3,3'-dimethoxy-4,4'-biphenylene)ditetrazolium salt; and
3-(4,5-dimethyl-2-thiazoyl)-2,5-diphenyl-2H-tetrazolium salt.

Further, tetrazolium compounds having ring substituents with a benzene ring structure at two positions and one substituent not having a ring structure at one position on its tetrazole ring also can be used. Examples of such tetrazolium compounds include:
2,3-diphenyl-5-cyano tetrazolium salt;
2,3-diphenyl-5-carboxy tetrazolium salt;
2,3-diphenyl-5-methyltetrazolium salt; and
2,3-diphenyl-5-ethyl tetrazolium salt.

Among the above-described tetrazolium compounds, preferable are those having three ring substituents as described above, and more preferable are those having three ring substituents with a benzene ring structure and having many electron-withdrawing functional groups. Particularly preferable is 2-(4-iodophenyl)-3-(2,4-dinitrophenyl)-5-(2,4-disulfophenyl)-2H-tetrazolium salt. It is to be noted here that the above-described tetrazolium compounds may be salts or may have been ionized, for example. Moreover, the tetrazolium compound may be used either alone or in combinations of two or more types.

The solution prepared so as to prevent the erroneous color development of DA-64 as described above can be used as a DA-64 reagent solution. The application of the DA-64 reagent solution is not particularly limited. For example, it can be used as a color-developing substrate reagent solution in a redox reaction described later, for example.

Hereinafter, the measurement method using a redox reaction according to the present invention will be described in detail with reference to the following example, in which a glycated protein in blood cells is measured.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited, and can be, for example, a method using a surfactant, a method using ultrasonic waves, and a method utilizing the difference in osmotic pressure. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are Triton X-100, Tween-20, Brij 35, and the like. The conditions of the treatment with the surfactant usually are as follows: when the concentration of blood cells in the solution to be treated is in the range from 1 to 10 vol %, the surfactant is added so that its concentration in the solution falls in the range from 0.01 to 5 wt %, and stirred at room temperature for about several seconds (about 5 seconds) to 10 minutes.

Next, a surfactant is added to the hemolyzed sample. In the case where the hemolyzed sample was prepared by causing the hemolysis using the surfactant as described above, it is not necessary to further add the surfactant if the concentration of the surfactant in the sample already is within the following range. On the other hand, if the concentration of the surfactant does not reach the following range, the surfactant may be added so as to make up a shortfall.

The surfactant may be added so that its final concentration in a reaction solution of a redox reaction described later falls in the range from 0.006 to 80 mmol/l, preferably from 0.05 to 40 mmol/l, and particularly preferably from 0.2 to 20 mmol/l. Furthermore, in the hemolyzed sample to which the surfactant has been added, the concentration of the surfactant is, for example, in the range from 0.1 to 200 mmol/l, preferably from 0.5 to 100 mmol/l, and particularly preferably from 2 to 100 mmol/l.

Subsequently, a tetrazolium compound and sodium azide further are added to the hemolyzed sample containing the surfactant.

The tetrazolium compound and the sodium azide may be added so that their final concentrations in the reaction solution of the redox reaction fall within the following ranges: the tetrazolium compound in the range from 0.01 to 40 mmol/l and the sodium azide in the range from 0.015 to 20 mmol/l; preferably, the tetrazolium compound in the range from 0.1 to 32 mmol/l and the sodium azide in the range from 0.05 to 12 mmol/l; and particularly preferably, the tetrazolium compound in the range from 0.15 to 24 mmol/l and the sodium azide in the range from 0.05 to 8 mmol/l.

Furthermore, the tetrazolium compound (A) and the sodium azide (B) are added so that they are present at a ratio (molar ratio A:B), for example, in the range from 10:1 to 1:1, preferably from 6:1 to 1.5:1, and more preferably from 4:1 to 2:1.

Specifically, when the concentration of blood cells in the solution to be treated is in the range from 1 to 10 vol %, for example, the tetrazolium compound preferably is added so that its concentration in the solution falls in the range from 0.02 to 2000 mmol/l, more preferably from 0.1 to 1000 mmol/l, and particularly preferably from 0.4 to 200 mmol/l. On the other hand, when the concentration of blood cells in the solution to be treated is in the range from 1 to 10 vol %, for example, the sodium azide preferably is added so that its concentration in the solution falls in the range from 0.006 to 800 mmol/l, more preferably from 0.04 to 400 mmol/l, and particularly preferably from 0.1 to 80 mmol/l.

The tetrazolium compound and the sodium azide may be added to the hemolyzed sample simply as they are. However, in terms of simplicity in operation etc., it is preferable to use a tetrazolium compound solution obtained by dissolving the tetrazolium compound in a solvent and a sodium azide solution obtained by dissolving the sodium azide in a solvent, or to use a liquid mixture containing both the tetrazolium compound and sodium azide (i.e., a tetrazolium compound-sodium azide liquid mixture).

As the solvent of the above-described solutions, MOPS, CHES, Tris-HCl, sodium phosphate, potassium phosphate, HEPES, TES buffers, and the like can be used, for example. The pH of the solvent is, for example, in the range from 5 to 12, preferably from 6 to 10.

Moreover, the tetrazolium compound-sodium azide liquid mixture prepared preferably is left for a certain period before being added to the hemolyzed sample so as to be aged, because this allows still further improvement in sensitivity. According to this aging treatment, the sensitivity becomes, for example, about 1.2 to 3 times greater than in the case where the aging treatment is not performed.

In the aging treatment, the treatment temperature preferably is in the range from 4° C. to 80° C., more preferably from 25° C. to 75°, and particularly preferably from 40° C. to 700, and the treatment period is, for example, in the range from 10 minutes to 200 hours, more preferably from 1 to 180 hours, and particularly preferably from 3 to 100 hours.

After the tetrazolium compound and sodium azide are added to the hemolyzed sample simply as they are or as the above-described solution, the pretreatment of the hemolyzed sample usually is carried out by incubating the sample at 10° C. to 40° C. for 1 to 10 minutes. By pretreating the sample with the tetrazolium compound, the influence of reducing substances and the like contained in the sample on a redox reaction can be eliminated, whereby the accuracy of measurement is improved. As described above, the tetrazolium compound contributes to the improvement in the accuracy of measurement by eliminating the influence of the reducing substances. In addition, when the tetrazolium compound is present with sodium azide, the measurement sensitivity also is improved.

Next, the pretreated hemolyzed sample containing the tetrazolium compound and sodium azide is treated with a protease. This protease treatment is carried out so that a FAOD used in the subsequent treatment can act on the analyte more easily.

The type of the protease is not particularly limited, and for example, serine proteases, thiol proteases, metalloproteinases, and the like can be used. Specifically, trypsin, proteinase K, chymotrypsin, papain, bromelain, subtilisin, elastase, aminopeptidase, and the like are preferable. In the case where the glycated protein to be degraded is glycated hemoglobin, the protease is the one that degrades the glycated hemoglobin selectively, and bromelain, papain, trypsin derived from porcine pancreas, metalloproteinases, and protease derived from *Bacillus subtilis*, and the like are preferable. Examples of the protease derived from *Bacillus subtilis* include a product named Protease N (e.g., Fluka Chemie AG) and a product named Protease N "AMANO" (Amano Enzyme Inc.). Examples of the metalloproteinases include metalloproteinase (EC 3. 4. 24. 4) derived from the genus *Bacillus*. Among these, metalloproteinases, bromelain, and papain are more preferable, and metalloproteinases are particularly preferable. Thus, a degradation product of a specific protein can be prepared selectively by using a protease that degrades the protein selectively. The protease treatment usually is carried out in a buffer, and the conditions of the treatment are determined as appropriate depending on the type of the protease used, the type and the concentration of the glycated protein as an analyte, etc.

As the buffer, CHES, CAPSO, CAPS, phosphate, Tris, EPPS, HEPES buffers, and the like can be used, for example. The pH of the buffer is, for example, in the range from 6 to 13, preferably from 7 to 10. Moreover, the final concentration of the buffer in the solution subjected to the protease treatment is, for example, in the range from 1 to 200 mmol/l.

Specifically, when the pretreated hemolyzed sample is treated using a metalloproteinase as the protease, the protease treatment usually is carried out under the conditions as follows: the concentration of the metalloproteinase in the reaction solution in the range from 2 to 20,000 KU/I; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12.

Furthermore, when the pretreated hemolyzed sample is treated using proteinase K as the protease, the protease treatment usually is carried out under the conditions as follows: the concentration of the protease in the reaction solution in the range from 1 to 10,000 KU/1; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12. Moreover, the type of the buffer is not particularly limited, and for example, Tris-HCl, EPPS, PIPES buffers, and the like can be used.

Next, the degradation product obtained by the protease treatment is treated with the FAOD. The reaction shown by Formula (1) above is catalyzed by this FAOD treatment.

Similarly to the above-described protease treatment, this FAOD treatment preferably is carried out in a buffer. The conditions of the FAOD treatment are determined as appropriate depending on the type of the FAOD used, the type and the concentration of the glycated protein as an analyte, etc.

Specifically, the FAOD treatment is carried out, for example, under the conditions as follows: the concentration of the FAOD in the reaction solution in the range from 50 to 50,000 U/1, the concentration of the blood cells in the reaction solution in the range from 0.01 to 1 vol %, the reaction temperature in the range from 15° C. to 37° C., the reaction period in the range from 1 to 60 minutes, and the pH in the range from 6 to 9. Moreover, the type of the buffer is not particularly limited, and the same buffers as in the protease treatment also can be used in the FAOD treatment.

Next, the hydrogen peroxide formed by the FAOD treatment is measured by a redox reaction using a POD and DA-64.

The DA-64 as a color-developing substrate may be added so that its final concentration in the reaction solution of the redox reaction falls in the range from 0.001 to 20 mmol/l, preferably from 0.005 to 2 mmol/l, and particularly preferably from 0.01 to 0.5 mmol/l.

The DA-64 (C) and the already added surfactant (D), tetrazolium compound (E), and sodium azide (F) are present at a ratio (molar ratio C:D:E:F), for example, in the range from 1:6:10:3 to 1:2000:1000:500, preferably from 1:10:20:10 to 1:1000:800:300, and more preferably from 1:40:30:10 to 1:500:600:200.

The pH of this reaction solution is in the range from 6 to 9, preferably from 6 to 8.

The redox reaction usually is carried out in a buffer. The conditions of the reaction are determined as appropriate depending on the concentration of the hydrogen peroxide formed, etc. Specifically, the conditions are, for example, as follows: the concentration of the POD in the reaction solution in the range from 10 to 100,000 IU/1; the concentration of the color-developing substrate in the range from 0.001 to 20 mmol/l; the reaction temperature in the range from 15° C. to 37° C.; the reaction period in the range from 0.1 to 30 minutes; and the pH in the range from 6 to 8. Moreover, the type of the buffer is not particularly limited, and for example, the same buffers as in the protease treatment and the FAOD treatment can be used.

The DA-64 develops color by a redox reaction. Thus, by measuring the absorbance (i.e., the degree of the color developed) of the reaction solution with a spectrophotometer at a wavelength, for example, in the range from 650 to 760 nm, the amount of the hydrogen peroxide can be determined. Then, using the amount of the hydrogen peroxide thus determined and a previously prepared calibration curve showing the correlation between an amount of hydrogen peroxide and an amount of glycated protein, the amount of the glycated protein in the sample can be determined.

Thus, by adding a surfactant in addition to a tetrazolium compound and sodium azide and setting the ratio of these components in the above-described range, the erroneous color development of DA-64 can be prevented. As a result, an increase in background can be suppressed so that high measurement accuracy can be realized.

Furthermore, as described above, the analyte is not particularly limited as long as a redox reaction is utilized. Examples of the analyte other than the glycated protein include glycated peptides, glycated amino acids, glucose, cholesterol, uric acid, creatinine, sarcosine, and glycerol. When the amount of each of the above-described examples of the analyte is measured, measurement can be carried out, for example, by forming an oxidizing substance derived from the analyte and measuring the amount of the oxidizing substance using a redox reaction in the same manner as described above.

For example, when the measurement is carried out by forming hydrogen peroxide as an oxidizing substance derived from the analyte, the hydrogen peroxide may be formed, for example, by action of: a glucose oxidase on the glucose; a cholesterol oxidase on the cholesterol; a uricase on the uric acid; a sarcosine oxidase on the creatinine; a sarcosine oxidase on the sarcosine; or a glycerol oxidase on the glycerol; respectively. The amount of the hydrogen peroxide can be measured in the same manner as above. Moreover, glycated peptides and glycated amino acids can be measured, for example, in the same manner as in the measurement of the glycated protein described above.

EXAMPLES (Treatment Solution A)
A-1: 40 mmol/l CHES buffer (pH 9.5) containing 7 g/l (12 mmol/l) of polyoxyethylene (9) lauryl ether (PEGLE)
A-2: 40 mmol/l CHES buffer (pH 9.5) containing 50 g/l (85 mmol/l) of PEGLE (Treatment Solution B)
A mixture containing 5 mmol/l of 2-(4-iodophenyl)-3-(2,4-dinitrophenyl)-5-(2,4-disulfophenyl)-2H-tetrazolium salt (product name WST3, manufactured by Dojindo Laboratories) and 1.5 mmol/i of sodium azide was prepared and incubated at 50° C. for 24 hours. Then, 3 ml of this mixture, 1 ml of a metalloproteinase (ARKRAY, Inc., 10,000 KU/1), 1 ml of MES buffer (50 mmol/l, pH 5.5), NaCl solution (500 mmol/l), and 3 ml of purified water were mixed with each other. The resultant mixture was used as a treatment solution B.

| (Treatment Solution C) | | | |
|---|---|---|---|
| C-1: | DA-64 | 80 | μmol/l |
| | Tris buffer (pH 7.0) | 300 | mmol/l |
| | FAOD (ARKRAY, INC.) | 30 | KU/l |
| | POD | 100 | KU/l |
| C-2: | DA-64 | 1000 | μmol/l |
| | Tris buffer (pH 7.0) | 300 | mmol/l |
| | FAOD (ARKRAY, INC.) | 30 | KU/l |
| | POD | 100 | KU/l |

(Procedure)
Blood was centrifuged (3000 rpm), and blood cells were collected. Then, 10 μl of the blood cells were mixed with 300 μl of the treatment solutions A (A-1 and A-2), respectively, to prepare hemolyzed samples. Then, 100 μl of the treatment solution B was added to 10 μl of these hemolyzed samples, and the resultant mixtures were incubated at 37° C. for 5 minutes. Subsequently, 22 μl of the treatment solutions C(C-1 and C-2) respectively were added to each of the mixtures, and the resultant mixtures were incubated at 37° C. The absorbance (at the wavelength of 751 nm) of these reaction solutions was measured using an automatic analysis apparatus named JCA-BM 8 (manufactured by Japan Electron Optics Laboratory Co. Ltd.). The instant at which the hemolyzed samples were mixed with the treatment reagent B was regarded as 0 second, and the instant at which the treatment solutions C were added was 300 seconds. In order to measure the erroneous color development occurring continuously after the completion of the reaction between the FAOD and the POD, the amount of change in absorbance between 486 seconds and 603 seconds was determined. Table 1 below shows the final concentrations of the respective components in the reaction solutions and the amount of the respective components relative to 1 μmol of the DA-64. Furthermore, FIG. 1 and Table 2 below show the results of the determination of the amount of the change in absorbance. FIG. 1 is a graph showing the change in absorbance of the reaction solution with time.

TABLE 1

| | Ex. 1 | Com. Ex. 1 | Com. Ex. 2 | Com. Ex. 3 |
|---|---|---|---|---|
| Treatment solution A | A-1 | A-2 | A-1 | A-2 |
| Treatment solution B | B | B | B | B |
| Treatment solution C | C-1 | C-1 | C-2 | C-2 |
| Final concentration during reaction | | | | |
| PEGLE (mmol/l) | 0.909 | 6.44 | 0.909 | 6.44 |
| WST-3 (mmol/l) | 1.136 | 1.136 | 1.136 | 1.136 |
| NaN$_3$ (mmol/l) | 0.341 | 0.341 | 0.341 | 0.341 |
| DA-64 (μmol/l) | 13.3 | 13.3 | 166.7 | 166.7 |
| Amount of respective components | | | | |
| PEGLE (mmol/l) | 0.068 | 0.483 | 0.005 | 0.039 |
| WST-3 (mmol/l) | 0.085 | 0.085 | 0.0068 | 0.0068 |
| NaN$_3$ (mmol/l) | 0.026 | 0.026 | 0.0020 | 0.0020 |
| DA-64 (μmol/l) | 1.0 | 1.0 | 1.0 | 1.0 |

TABLE 2

| | Ex. 1 | Com. Ex. 1 | Com. Ex. 2 | Com. Ex. 3 |
|---|---|---|---|---|
| Amount of change in absorbance | 0.0049 | 0.0091 | 0.0087 | 0.0099 |

As shown in Table 1 above, in Comparative Example 1, the amount of the PEGLE was too large (>0.4 mmol) relative to 1 μmol of the DA-64. In Comparative Example 2, the amounts of the PEGLE (<0.006 mmol), the WST-3 (<0.01 mmol), and the NaN$_3$ (<0.003 mmol) were too small relative to 1 μmol of the DA-64, and in Comparative Example 3, the amounts of the WST-3 (<0.01 mmol) and the NaN$_3$ (<0.003 mmol) were too small relative to 1 μmol of the DA-64. Thus, Comparative Examples 1 to 3 exhibited high absorbance owing to the erroneous color development as shown in FIG. 1, and thus the amount of the change in absorbance was considerable as shown in Table 2. In contrast, in Example 1, since the erroneous color development was prevented, the absorbance was low as shown in FIG. 1 and thus the amount of the change in absorbance was reduced. These results demonstrate that the method of the present invention can prevent the erroneous color development of DA-64, thereby improving the accuracy of measurement.

INDUSTRIAL APPLICABILITY

As specifically described above, according to the present invention, erroneous color development of DA-64 as a color-developing substrate can be prevented. Therefore, by applying the method of preventing the erroneous color development to measurement using a redox reaction, an increase in background due to the erroneous color development can be suppressed so that the accuracy of the measurement can be improved. Moreover, by applying such a measurement method to, for example, the measurement of HbA1c in erythrocytes, it becomes possible to realize measurement with higher accuracy than in conventional methods, which further increases the importance of HbA1c as an indicator in the diagnosis and the like of diabetes.

The invention claimed is:

1. A method of measuring an oxidizing substance derived from an analyte in a sample, comprising:
    causing a reaction between the oxidizing substance derived from the analyte and N-(carboxymethylaminocarbonyl)-4,4'-bis(dimethylamino)diphenylamine sodium salt as a substrate that develops color as a result of the reaction, the reaction being caused by an oxidoreductase in the presence of a tetrazolium compound and sodium azide, the N-(carboxymethylaminocarbonyl)-4,4'-bis(dimethylamino)diphenylamine sodium salt, the tetrazolium compound and the sodium azide being present in an aqueous solution with a surfactant; and
    determining an amount of the oxidizing substance by measuring the color developed by the substrate,
    the method farther comprising, before the step of causing a reaction, determining an amount of the tetrazolium compound, the sodium azide, and the surfactant, and a pH of the solution, that will reduce erroneous color formation of the N-(carboxymethylaminocarbonyl)-4,4'-bis(dimethylamino)diphenylamine sodium salt as a result of the reaction, and
    mixing the tetrazolium compound and the sodium azide in the determined amounts with the N-(carboxymethylaminocarbonyl)-4,4'-bis(dimethylamino)diphenylamine sodium salt in the presence of the determined amount of the surfactant in an aqueous solvent,
    wherein the determined amounts are selected to provide concentrations in the mixture in the ranges of 0.01 to 1 mmol of the tetrazolium compound, 0.003 to 0.5 mmol of the sodium azide, and 0.006 to 0.4 mmol of the surfactant, per µmol of the N-(carboxymethylaminocarbonyl)-4,4'-bis(dimethylamino)diphenylamine sodium salt, and the pH of the mixture is in a range of 6 to 9.

2. The method according to claim 1, wherein the aqueous solvent is a sample solution containing the analyte.

3. The method according to claim 2, wherein the tetrazolium compound and the sodium azide arc added to the sample solution and thereafter, the N-(carboxymethylamino carbonyl)-4,4'-bis(dimethylwnino)dipheaylamine sodium salt and the oxidoreductase further are added to the sample solution in the presence of the surfactant to cause the reaction by the oxidoreductase.

4. The method according to claim 3, wherein the analyte is treated with a protease prior to the reaction caused by the oxidoreductase.

5. The method according to claim 4, wherein the oxidoreductase is caused to act on a degradation product of the analyte obtained by the treatment with the protease.

6. The method according to claim 1, wherein the oxidoreductase is a fructosyl amino acid oxidase.

7. The method according to claim 1, wherein the oxidizing substance derived from the analyte is hydrogen peroxide.

8. The method according to claim 1, wherein the analyte is a glycated protein.

9. The method according to claim 8, wherein the analyte is glycated hemoglobin.

10. The method according to claim 1, wherein the tetrazolium compound is 2-(4-iodophenyl)-3-(2,4-dinitrophenyl)-5-(2,4-disulfophenyl)-2H-tetrazolium salt.

* * * * *